United States Patent [19]

Hoshino et al.

[11] Patent Number: 4,863,987

[45] Date of Patent: Sep. 5, 1989

[54] DEODORIZING COATING FORMULATIONS AND DEODORIZING SHEETS MAKING USE OF SAME

[75] Inventors: Akira Hoshino, Koshigaya; Mikio Saji, Kasukabe; Shigeaki Fujii, Washinomiya, all of Japan

[73] Assignee: Dainichiseika Color & Chemicals Mfg. Co., Ltd., Tokyo, Japan

[21] Appl. No.: 928,381

[22] Filed: Nov. 10, 1986

[30] Foreign Application Priority Data

Apr. 7, 1986 [JP] Japan .................. 61-078184
Apr. 7, 1986 [JP] Japan .................. 61-078185
Apr. 7, 1986 [JP] Japan .................. 61-078186
May 13, 1986 [JP] Japan .................. 61-107544

[51] Int. Cl.$^4$ .................. C08L 33/08; C08L 33/10
[52] U.S. Cl. .................. 524/293; 106/181; 424/642; 524/294; 524/295; 524/296; 524/298; 524/300; 524/320; 524/321; 524/423
[58] Field of Search .................. 106/35, 181; 524/423, 524/293, 294–296, 298, 300, 320, 321; 428/145; 252/42

[56] References Cited

U.S. PATENT DOCUMENTS

| | | | |
|---|---|---|---|
| 4,138,477 | 2/1979 | Gaffar | 424/56 |
| 4,166,744 | 9/1979 | Smith | 106/35 |
| 4,454,050 | 6/1984 | Bertell | 252/42 |
| 4,565,693 | 1/1986 | Marschner | 424/67 |

Primary Examiner—Theodore Morris
Attorney, Agent, or Firm—Oblon, Fisher, Spivak, McClelland & Maier

[57] ABSTRACT

A deodorizing coating formulation is composed of a white or substantially colorless deodorizing agent, a binder resin and a liquid medium. The deodorizing agent may preferably be composed of 10–90 parts by weight of a zinc compound and 90–10 parts by weight of an aliphatic polycarboxylic acid, aromatic polycarboxylic acid, acidic polymer or a sulfate of aluminum, or a salt thereof. A deodorizing sheet can be obtained by coating and/or impregnating a base sheet with the deodorizing coating formulation and then drying the resulting base sheet. The deodorizing sheet can shield a flavor or odor from external flavors or odors while maintaining air permeability, it is suitable for wrapping foods having strong flavors or odors.

18 Claims, No Drawings

DEODORIZING COATING FORMULATIONS AND DEODORIZING SHEETS MAKING USE OF SAME

BACKGROUND OF THE INVENTION

1. Field of the Invention

This invention relates to deodorizing coating formulations and deodorizing sheets making use of same, and more specifically to deodorizing coating formulations and deodorizing sheets making use of same, which are useful for coating various food containers or wrapping foods or for other deodorizing purposes.

2. Description of the Prior Art

As packages for various foods, especially, foods having strong flavors or odors and other articles, there have been primarily used containers having no air permeability such as metal, plastic or glass containers and for simple packaging, wrapping sheets having no air permeability (for example, aluminum foils and plastic sheets). A wide variety of deodorizers are also used where offensive unpleasant odors tend to remain at high concentrations, such as car interiors, toilets, refrigerators, etc.

Such various conventional containers or wrapping sheets, which have been employed to package foods and the like, are intended to prevent loss of flavors from foods and the like, lingering of external flavors or odors or emission of flavors or odors of contents. In general, they are all more costly compared with general wrapping sheets. Where air permeability is required for packaging materials like those employed to package perishable foods as contents, conventional containers or wrapping sheets having no air permeability cannot be used. Air-permeable containers or wrapping sheets are however ineffective for the prevention of leakage of flavors or odors of foods into the surrounding atmosphere or lingering of external flavors or odors to packaged foods. It is also undesirable from the viewpoint of beauty or space saving to place put-up deodorizers in car interiors or the like.

There is hence a strong outstanding demand for the development of wrapping sheets, which permit permeation of air therethrough from and into the surrounding atmosphere but shut off flavors or odors only and are hence useful as wrapping materials for various foods, as well as deodorizers not showing mismatching appearance in rooms.

SUMMARY OF THE INVENTION

The present inventors have carried out an extensive investigation with a view toward meeting the aforementioned demand. As a result, it has been found that such an outstanding demand can be fulfilled by applying a certain specific material to general wrapping sheets or packaging containers or other articles, leading to completion of this invention.

In one aspect of this invention, there is thus provided a deodorizing coating formulation which comprises a deodorizing ingredient, a binder resin and a liquid medium. The deodorizing ingredient is a white or substantially colorless deodorizing agent.

In another aspect of this invention, there is also provided a deodorizing sheet by coating and/or impregnating a base sheet with the above deodorizing coating formulation and then drying the resulting base sheet.

Since the deodorizing sheet can shield a flavor or odor from external flavors or odors while maintaining air permeability, it is suitable for packaging or wrapping foods having strong flavors or odors. For example, the flavors or odors of several foods of different kinds are not allowed to mix together even if they are stored at the same place (for example, in a refrigerator) subsequent to their packaging or wrapping with the deodorizing sheet of this invention. The deodorizing sheet of this invention is therefore useful particularly for packaging or wrapping such foods.

In addition, the deodorizing sheet of this invention may also be used as wall paper in a car interior or toilet, as wall paper or flooring in odor-filled work room or for like purposes, whereby it can achieve the intended object of deodorization without impairing the beauty of these rooms or presenting mismatching appearance.

The deodorizing coating formulation and deodorizing sheet of this invention are effective not only for unpleasant odor components of the amine type but also for sulfur-containing unpleasant odor components.

The above and other objects, features and advantages of this invention will become apparent from the following description and the appended claims.

DETAILED DESCRIPTION OF THE INVENTION AND PREFERRED EMBODIMENTS

Principal features of this invention reside in that certain specific compounds are used in combination as a deodorizing ingredient and an organic or inorganic liquid medium is used as a liquid medium.

Although it has been known in the prior art to use a ferrous salt or activated carbon as a deodorizing ingredient of a deodorizer, use of such a ferrous salt is accompanied by a drawback that when prepared into a coating formulation, the ferrous salt causes the resultant coating formulation to gel because the ferrous salt is reactive with a binder resin also contained in the coating formulation. Where the binder resin of the coating formulation is a vinyl chloride resin, the ferrous salt has another drawback that the ferrous salt accelerates dechlorination of the vinyl chloride resin and hence deteriorates the coating film. Furthermore, when a variety of paper, plastic sheets, woven fabric, non-woven fabric or their composite materials are coated and/or impregnated with the above ferrous salt and are then dried under heat, the ferrous salt undergoes discoloration and stains base sheets in a brown color. Its deodorizing effects are therefore reduced, the application of other colors or decoration is rendered difficult, and the commercial values of sheets, notably, those bearing various prints are significantly lowered. On the other hand, use of activated carbon result in black coating formulations, thereby making it impossible to apply other colors.

In the present invention, a white or substantially colorless zinc compound is employed in lieu of such a ferrous salt or activated carbon and an organic acid such as aliphatic polycarboxylic acid or a salt thereof or both of them are used in combination with the zinc compound, so that the deodorizing coating formulation and deodorizing sheet of this invention are effective for the deodorization of not only unpleasant odor components of the amine type but also sulfur-containing unpleasant odor components. The deodorizing sheet of this invention is not stained into a brown color upon its drying. It has also been found that the zinc compound and the aliphatic polycarboxylic acid or its salt exhibit synergistic deodorizing effects greater than the sum of their respective deodorizing effects. Owing to the use of the above-described deodorizing ingredient, the deodorizing coating formulation of this invention is not tinged into a black or brown color. It is therefore possible to color the deodorizing coating formulation into a desired color tone with one or more other coloring agents.

The individual deodorizing agents useful in the practice of this invention are themselves all known compounds. As the zinc compound, any one of various zinc compounds may be employed, for example, an inorganic zinc compound such as zinc oxide, zinc sulfate, zinc chloride, zinc phosphate, zinc nitrate or zinc carbonate, or an organic zinc salt such as zinc acetate, zinc oxalate, zinc citrate, zinc fumarate or zinc formate, with zinc flower (zinc oxide) or zinc carbonate being particularly preferred.

Illustrative examples of the aliphatic polycarboxylic acid useful in the practice of this invention may include di- and tri-carboxylic acids such as oxalic acid, malonic acid, succinic acid, glutaric acid, adipic acid, pimelic acid, fumaric acid, maleic acid, methylmaleic acid, methylfurmaric acid, itaconic acid, citraconic acid, mesaconic acid, acetylenic acid, malic acid, methylmalic acid, citric acid, isocitric acid and tartaric acid as well as their salts. In the present invention, citric acid or fumaric acid or its salt is especially preferred.

The term "aromatic carboxylic acid or a salt thereof" as used herein includes, for example, phthalic acid, terephthalic acid, isophthalic acid, trimellitic acid, 1,2,3-benzenetricarboxylic acid, pyromellitic acid, benzenehexacarboxylic acid, naphthalenedicarboxylic acid, naphthalenetricarboxylic acid, naphthalenetetracarboxylic acid, diphenyltetracarboxylic acid and azobenzenetetracarboxylic acid, as well as their anhydrides and salts. It is trimellitic acid or its salt that is particularly preferred in the present invention.

The term "acidic polymer" as used herein means a polymer containing sulfonic groups, carboxylic groups, sulfuric ester groups, phosphoric ester groups or phenolic hydroxyl groups in its molecule. It may, for example, include the following polymers.

(a) Polymers containing carboxylic groups:

Polyesters with terminal carboxyl groups, obtained by reacting polycarboxylic acids such as citric acid, tartaric acid and phthalic acid and polyhydric alcohols such as ethylene glycol, 1.4-butanediol and diethylene glycol while using the acids in excess amounts;

Acidic cellulose derivatives modified by various polycarboxylic acids;

Homopolymers of vinyl ether ester monomers and the like of polycarboxylic acids, and random copolymers, block copolymers, graft copolymers and like of the vinyl ether ester monomers and and other general monomers;

Homopolymers of monomers such as acrylic acid and methacrylic acid and random copolymers, block copolymers, graft copolymers and like of the monomers and other general monomers; Homopolymers of $\alpha,\beta$-unsaturated vinyl monomers such as maleic anhydride and itaconic acid, and random copolymers, block copolymers, graft copolymers and like of the vinyl monomers;

(b) Polymers containing sulfonic groups:

Cellulose derivatives such as ethyl cellulose, hydrogenacetate hydrogensulfate phthalate, cellulose hydrogenacetate hydrogensulfate phthalate, ethyl cellulose hydrogensulfobenzoate, sulfonbenzyl cellulose acetate and ethyl sulfoethyl cellulose acetate; Sulfonic acid modified polymers obtained by modifying polyvinyl alcohol or vinyl alcohol copolymers with sulfonic acid compounds (for example, o-sulfobenzoic acid, sulfopropionic acid, sulfovaleric acid, sulfobenzaldehyde, sulfophthalic acid, etc.); and (c) Polymers containing hydroxyl groups:

Homopolymers of other sulfonic acids or phenolic group containing monomers, and random copolymers, block copolymers, graft copolymers and like of the other sulfonic acids or phenolic group containing monomers;

Besides, may also be mentioned acid modified products obtained by modifying various polymers with carboxyl carboxyl, sulfonic or phenolic group containing compounds.

Of these, carboxyl-containing polymers are particularly preferred.

The term "sulfate of aluminum" as used herein include aluminum sulfate $[Al_2(SO_4)_3]$ and potassium aluminum sulfate $[KAl(SO_4)_3]$ with aluminum sulfate being especially preferred.

In the deodorizing ingredient composed of a zinc compound and an aliphatic polycarboxylic acid or the like or a salt thereof such as those described above, their proportions are also important. Supposing the the total amount is 100 parts by weight, the zinc compound is used in an amount of 10–90 parts by weight whereas the aliphatic polycarboxylic acid or the like or its salt is employed in an amount of 90–10 parts by weight. Such a combination and mixing ratio can best achieve the objects of this invention.

The deodorizing coating formulation of this invention can be obtained by mixing a deodorizing ingredient such as that mentioned above with a binder resin and a liquid medium.

As the binder resin, it is preferable to use an acrylic resin, a vinyl acetate base resin, or a resin employed as a binder resin in various conventional water-base or oil-base paints or printing inks. Such a binder resin may be either thermoplastic or thermosetting.

As the liquid medium, it is possible to use any one of water, alcohols, ketones, aromatic solvents, aliphatic solvents and other organic solvents or a mixture thereof.

The binder resin may be at any concentration. In general, about 10–30 wt.% or so is preferred. Such a binder resin may be in a state dissolved or dispersed or emulsified in the liquid medium.

The deodorizing coatingg formulation of this invention can be obtained by either dissolving or dispersing the above-described ingredient to a concentration of about 10–30 wt.% in the liquid medium containing such a conventionally-known binder resin.

Needless to say, one or more colorants such as dyes or pigments and other paint additives may also be incorporated in the deodorizing coating formulation of this invention as described above.

As described above, the deodorizing sheet of this invention can be obtained by coating and/or impregnating one side or both sides of a sheet such as general wrapping paper, plastic sheet, woven fabric or nonwoven fabric or their composite material with the deodorizing coating composition of this invention and then drying the resulting sheet.

As the sheet useful as a base material in the present invention, an air-permeable base material is preferred such as paper, perforated plastic sheet, fabric or nonwoven fabric. The present invention is however not necessarily limited to them. Paper having no air permeability, coated paper or plastic sheets may also be used.

Although no particular limitation is imposed on the amount of the deodorizing coating formulation with which a base material is to be coated and/or impregnated, it may generally be applied to an amount of about 5–20 g/m² in terms of solids or about 1–10 g/m² in terms of the deodorizing ingredient. By controlling the thus-applied amount within this range, it is possible to impart excellent deodorizing effects without losing the permeability of wrapping paper, plastic sheet, woven fabric, non-woven fabric or the like. Incidentally, the deodorizing coating formulation may be applied and dried by any methods known per se in the art.

This invention will hereinafter be described more specifically by the following Examples, in which all designations of "part or parts" and "%" mean part or parts by weight and wt.%.

EXAMPLE 1

A deodorizing coating formulation of this invention was obtained by dissolving 15 parts of a 10:3:1 mixture by weight of zinc oxide, fumaric acid and sodium fumarate in a mixture of 60 parts of a 3:1 mixed solvent of ethyl acetate and isopropyl alcohol and 25 parts of a 5:1 mixture of nitrocellulose and an alkyd resin.

The deodorizing coating formulation was then applied by a photogravure technique onto one side of a sheet of kraft paper to give a coat weight of 8 g/m² and the thus-coated paper sheet was dried to provide a deodorizing sheet of this invention. The deodorizing performance of the deodorizing sheet was tested in the following manner.

Deodorizing test on ammonia:

A 50 mm×200 mm sheet was cut off from the above deodorizing sheet and then folded double with its coated side out. A double-tack tape was then applied between the front and rear halves along the edges of the respective front and rear halves except for the crease in order to avoid influence of the uncoated side. The above-prepared sheet was then placed in a 300-ml Erlenmeyer flask, followed by an addition of 10 μl of 28% aqueous ammonia. The outlet of the flask was sealed with paraffin and the aqueous ammonia was allowed to gasify fully. The flask was thereafter stored at 25° C. and upon an elapse of a predetermined time period, the concentration (ppm) of ammonia in the flask was measured by a Kitagawa's probe. The following results were obtained.

| Lapsed time | 5 minutes | 30 minutes | 120 minutes |
|---|---|---|---|
| Blank | 4000 | 4000 | 4000 |
| Invention product | 2500 | 2000 | 1350 |
| Comparative Example | 3000 | 2500 | 1500 |

Deodorizing test on hydrogen sulfide:

A 50 mm×100 mm sheet was cut off from the above deodorizing sheet and then folded double with its coated side out. A double-tack tape was then applied between the front and rear halves along the edges of the respective front and rear halves except for the crease in order to avoid influence of the uncoated side. The above-prepared sheet was then placed in a 300-ml Erlenmeyer flask, followed by addition of 1 ml of an 800 ppm solution of sodium sulfide in water and 0.1 ml of 1N sulfuric acid. The outlet of the flask was sealed with paraffin and the resulting hydrogen sulfide was allowed to gasify fully. The flask was thereafter stored at 25° C. and upon an elapse of a predetermined time period, the concentration (ppm) of hydrogen sulfide in the flask was measured by a Kitagawa's probe. The following results were obtained.

| Lapsed time | 1 day | 2 days | 9 days |
|---|---|---|---|
| Blank | 150 | 150 | 150 |
| Invention product | 4 | trace | not detected |
| Comparative Example | 10 | 3 | 1 |

EXAMPLES 2–18

Deodorizing sheets of this invention were separately obtained in the same manner as in Example 1 except that the following ingredients were used. Following the procedure of Example 1, their performance was measured. Results are given below.

EXAMPLE 2

An 8:1.5:0.5 mixture of zinc carbonate, fumaric acid and potassium fumarate.

| | Deodorizing test on ammonia: | | |
|---|---|---|---|
| Lapsed time | 5 minutes | 30 minutes | 120 minutes |
| Blank | 4000 | 4000 | 4000 |
| Invention product | 2850 | 2350 | 1400 |
| Comparative Example | 3000 | 2500 | 1500 |

| | Deodorizing test on hydrogen sulfide: | | |
|---|---|---|---|
| Lapsed time | 1 day | 2 days | 9 days |
| Blank | 150 | 150 | 150 |
| Invention product | 1 | trace | not detected |
| Comparative Example | 10 | 3 | 1 |

EXAMPLE 3

An 8.5:1.5 mixture of zinc oxide and potassium citrate.

| | Deodorizing test on ammonia: | | |
|---|---|---|---|
| Lapsed time | 5 minutes | 30 minutes | 120 minutes |
| Blank | 4000 | 4000 | 4000 |
| Invention product | 3000 | 2000 | 1700 |
| Comparative Example | 3000 | 2500 | 1500 |

| | Deodorizing test on hydrogen sulfide: | | |
|---|---|---|---|
| Lapsed time | 1 day | 2 days | 9 days |
| Blank | 150 | 150 | 150 |
| Invention product | trace | not detected | not detected |
| Comparative Example | 10 | 3 | 1 |

EXAMPLE 4

An 8.7:1.3 mixture of zinc carbonate and fumaric acid.

| Deodorizing test on ammonia: | | | |
|---|---|---|---|
| Lapsed time | 5 minutes | 30 minutes | 120 minutes |
| Blank | 4000 | 4000 | 4000 |
| Invention product | 2500 | 1800 | 1300 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | trace | not detected | not detected |
| Comparative Example | 10 | 3 | 1 |

EXAMPLE 5

Fifteen parts of a 10:3:1 mixture by weight of zinc oxide, trimellitic acid and sodium trimellitate.

| Deodorizing test on ammonia: | | | |
|---|---|---|---|
| Lapsed time | 5 minutes | 30 minutes | 120 minutes |
| Blank | 4000 | 4000 | 4000 |
| Invention product | 2500 | 2000 | 1300 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | 3 | trace | not detected |
| Comparative Example | 10 | 3 | 1 |

EXAMPLE 6

An 8:1.5:0.5 mixture of zinc carbonate, trimellitic acid and potassium trimellitate.

| Deodorizing test on ammonia: | | | |
|---|---|---|---|
| Lapsed time | 5 minutes | 30 minutes | 120 minutes |
| Blank | 4000 | 4000 | 4000 |
| Invention product | 2850 | 2200 | 1400 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | 1 | not detected | not detected |
| Comparative Example | 10 | 3 | 1 |

EXAMPLE 7

An 8.5:1.5 mixture of zinc oxide and naphthalenetricarboxylic acid.

| Deodorizing test on ammonia: | | | |
|---|---|---|---|
| Lapsed time | 5 minutes | 30 minutes | 120 minutes |
| Blank | 4000 | 4000 | 4000 |
| Invention product | 2900 | 1850 | 1400 |
| Comparative | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | 1 | not detected | not detected |
| Comparative Example | 10 | 3 | 1 |

EXAMPLE 8

An 8.7:1.3 mixture of zinc carbonate and trimellitic acid.

| Deodorizing test on ammonia: | | | |
|---|---|---|---|
| Lapsed time | 5 minutes | 30 minutes | 120 minutes |
| Blank | 4000 | 4000 | 4000 |
| Invention product | 3100 | 2300 | 1400 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | not detected | not detected | not detected |
| Comparative Example | 10 | 3 | 1 |

EXAMPLE 9

A 10:3 mixture of zinc oxide and a carboxylic acid polymer.

| Deodorizing test on ammonia: | | | |
|---|---|---|---|
| Lapsed time | 5 minutes | 30 minutes | 120 minutes |
| Blank | 4000 | 4000 | 4000 |
| Invention product | 2500 | 2000 | 1300 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | 3 | trace | not detected |
| Comparative Example | 10 | 3 | 1 |

EXAMPLE 10

An 8:2 mixture of ferrous sulfate and a carboxylic acid polymer ("TESKYD MRM43", trade name; product of Hitachi Kasei Polymer Co., Ltd., Tokyo, Japan).

| Deodorizing test on ammonia: | | | |
|---|---|---|---|
| Lapsed time | 5 minutes | 30 minutes | 120 minutes |
| Blank | 4000 | 4000 | 4000 |
| Invention product | 2850 | 2200 | 1400 |
| Comparative Example | 3000 | 2500 | 1500 |

| Deodorizing test on hydrogen sulfide: | | | |
|---|---|---|---|
| Lapsed time | 1 day | 2 days | 9 days |

-continued

| | | | |
|---|---|---|---|
| Blank | 150 | 150 | 150 |
| Invention product | 1 | not detected | not detected |
| Comparative Example | 10 | 3 | 1 |

EXAMPLE 11

An 8.5:1.5 mixture of zinc carbonate and an acidic polymer ("TESKYD MRA-A", trade name; product of Hitachi Kasei Polymer Co., Ltd., Tokyo, Japan).

| | Deodorizing test on ammonia: | | |
|---|---|---|---|
| Lapsed time | 5 minutes | 30 minutes | 120 minutes |
| Blank | 4000 | 4000 | 4000 |
| Invention product | 2900 | 2850 | 1400 |
| Comparative Example | 3000 | 2500 | 1500 |

| | Deodorizing test on hydrogen sulfide: | | |
|---|---|---|---|
| Lapsed time | 1 day | 2 days | 9 days |
| Blank | 150 | 150 | 150 |
| Invention product | 1 | not detected | not detected |
| Comparative Example | 10 | 3 | 1 |

EXAMPLE 12

An 8.7:1.3 mixture of zinc carbonate and a carboxylic acid polymer ("TESKYD MRA-L", trade name; product of Hitachi Kasei Polymer Co., Ltd., Tokyo, Japan).

| | Deodorizing test on ammonia: | | |
|---|---|---|---|
| Lapsed time | 5 minutes | 30 minutes | 120 minutes |
| Blank | 4000 | 4000 | 4000 |
| Invention product | 3100 | 2300 | 1400 |
| Comparative Example | 3000 | 2500 | 1500 |

| | Deodorizing test on hydrogen sulfide: | | |
|---|---|---|---|
| Lapsed time | 1 day | 2 days | 9 days |
| Blank | 150 | 150 | 150 |
| Invention product | not detected | not detected | not detected |
| Comparative Example | 10 | 3 | 1 |

EXAMPLE 13

A 6:4 mixture of aluminum sulfate and a carboxylic acid polymer ("NEW FRONTIER MI-400P", trade name; product of Dai-ichi Kogyo Seiyaku Co., Ltd., Kyoto, Japan).

| | Deodorizing test on ammonia: | | |
|---|---|---|---|
| Lapsed time | 5 minutes | 30 minutes | 120 minutes |
| Blank | 4000 | 4000 | 4000 |
| Invention product | 2850 | 2200 | 1400 |
| Comparative Example | 3000 | 2500 | 1500 |

| | Deodorizing test on hydrogen sulfide: | | |
|---|---|---|---|
| Lapsed time | 1 day | 2 days | 9 days |
| Blank | 150 | 150 | 150 |
| Invention product | 1 | not detected | not detected |
| Comparative Example | 10 | 3 | 1 |

EXAMPLE 14

An 5:3:2 mixture of zinc carbonate, aluminum sulfate and a acidic polymer ("TESKYD MRA43", trade name; product of Hitachi Kasei Polymer Co., Ltd., Tokyo, Japan).

| | Deodorizing test on ammonia: | | |
|---|---|---|---|
| Lapsed time | 5 minutes | 30 minutes | 120 minutes |
| Blank | 4000 | 4000 | 4000 |
| Invention product | 2900 | 1850 | 1400 |
| Comparative Example | 3000 | 2500 | 1500 |

| | Deodorizing test on hydrogen sulfide: | | |
|---|---|---|---|
| Lapsed time | 1 day | 2 days | 9 days |
| Blank | 150 | 150 | 150 |
| Invention product | 1 | not detected | not detected |
| Comparative Example | 10 | 3 | 1 |

EXAMPLE 15

A 7:3 mixture by weight of zinc oxide and aluminum sulfate.

| | Deodorizing test on ammonia: | | |
|---|---|---|---|
| Lapsed time | 5 minutes | 30 minutes | 120 minutes |
| Blank | 4000 | 4000 | 4000 |
| Invention product | 2600 | 2000 | 1400 |
| Comparative Example | 3000 | 2500 | 1500 |

| | Deodorizing test on hydrogen sulfide: | | |
|---|---|---|---|
| Lapsed time | 1 day | 2 days | 9 days |
| Blank | 150 | 150 | 150 |
| Invention product | 4 | trace | not detected |
| Comparative Example | 10 | 3 | 1 |

EXAMPLE 16

An 8:2 mixture of zinc carbonate and aluminum sulfate.

| | Deodorizing test on ammonia: | | |
|---|---|---|---|
| Lapsed time | 5 minutes | 30 minutes | 120 minutes |
| Blank | 4000 | 4000 | 4000 |
| Invention product | 2600 | 2100 | 1300 |
| Comparative Example | 3000 | 2500 | 1500 |

| | Deodorizing test on hydrogen sulfide: | | |
|---|---|---|---|
| Lapsed time | 1 day | 2 days | 9 days |
| Blank | 150 | 150 | 150 |
| Invention product | trace | not detected | not detected |
| Comparative | 10 | 3 | 1 |

EXAMPLE 17

A 5:5 mixture of zinc carbonate and aluminum sulfate.

| Deodorizing test on ammonia: | | | |
|---|---|---|---|
| Lapsed time | 5 minutes | 30 minutes | 120 minutes |
| Blank | 4000 | 4000 | 4000 |
| Invention product | 2400 | 1600 | 1100 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | 3 | trace | not detected |
| Comparative Example | 10 | 3 | 1 |

EXAMPLE 18

A 4:6 mixture of zinc oxide and aluminum sulfate.

| Deodorizing test on ammonia: | | | |
|---|---|---|---|
| Lapsed time | 5 minutes | 30 minutes | 120 minutes |
| Blank | 4000 | 4000 | 4000 |
| Invention product | 2300 | 1500 | 1000 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | 5 | trace | not detected |
| Comparative Example | 10 | 3 | 1 |

In each of the above Examples 1-18, a sheet obtained by using a coating formulation free of any deodorizing ingredient was used as the blank while a sheet obtained by using a coating formulation making use of ferrous sulfate alone was employed in the Comparative Example.

In addition, bags were produced respectively from the sheets employed as the blanks, invention products and comparative products in Examples 1-18. Thawed small fish was placed within the bags. The bags were left over and were then opened three days later. Little unpleasant odors were felt in the bags produced from the sheets of this invention, whereas strong unpleasant odors were emitted from the bags made of the blanks.

Furthermore, the bags made respectively of the comparative products were all stained in brown colors while those produced respectively from the invention products were not stained practically.

EXAMPLE 19

A deodorizing coating formulation of this invention was obtained by dissolving 20 parts of an 8:1.5:0.5 mixture of zinc chloride, citric acid and lithium citrate in a mixture of 60 parts of a 1:1 mixed solvent of toluene and methyl ethyl ketone and 20 parts of a vinyl chloride copolymer.

The deodorizing coating formulation was then applied by a photogravure technique onto one side of a polyester/polypropylene non-woven fabric to give a coat weight of 8 g/m² and the thus-coated fabric was dried to provide a deodorizing sheet of this invention.

A deodorizing test was then conducted on the deodorizing sheet in the same manner as in Example 1. The following results were obtained.

| Deodorizing test on ammonia: | | | |
|---|---|---|---|
| Lapsed time | 5 minutes | 30 minutes | 120 minutes |
| Blank | 4000 | 4000 | 4000 |
| Invention product | 3000 | 2300 | 1450 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | trace | not detected | not detected |
| Comparative Example | 10 | 3 | 1 |

Further, the following deodorizing ingredient was used instead of the above-described deodorizing ingredient. The following results were obtained.

(1) An 8:1.5:0.5 mixture of zinc chloride, naphthalenetricarboxylic acid and lithium naphthalenetricarboxylate.

| Deodorizing test on ammonia: | | | |
|---|---|---|---|
| Lapsed time | 5 minutes | 30 minutes | 120 minutes |
| Blank | 4000 | 4000 | 4000 |
| Invention product | 2700 | 2000 | 1400 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | trace | not detected | not detected |
| Comparative Example | 10 | 3 | 1 |

(2) A 7:3 mixture of zinc chloride and an acidic polymer ("TESKYD MRA-L", trade name; product of Hitachi Kasei Polymer Co., Ltd., Tokyo, Japan).

| Deodorizing test on ammonia: | | | |
|---|---|---|---|
| Lapsed time | 5 minutes | 30 minutes | 120 minutes |
| Blank | 4000 | 4000 | 4000 |
| Invention product | 2700 | 2000 | 1400 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | trace | not detected | not detected |
| Comparative Example | 10 | 3 | 1 |

(3) An 8:1.5:0.5 mixture of zinc chloride, aluminum sulfate and potassium aluminum sulfate

| Deodorizing test on ammonia: | | | |
|---|---|---|---|
| Lapsed time | 5 minutes | 30 minutes | 120 minutes |
| Blank | 4000 | 4000 | 4000 |
| Invention product | 2500 | 2000 | 1300 |
| Comparative Example | 3000 | 2500 | 1500 |

| Deodorizing test on hydrogen sulfide: | | | |
|---|---|---|---|
| Lapsed time | 1 day | 2 days | 9 days |
| Blank | 150 | 150 | 150 |
| Invention product | 3 | trace | not detected |
| Comparative Example | 10 | 3 | 1 |

By the way, the bag of the Comparative Example was stained in a brown color while that produced from the invention product was not stained practically.

EXAMPLE 20

The deodorizing coating formulations of Examples 1, 5, 9 and 15 were separately sprayed at a rate of 10 g/m$^2$ onto the inner walls of linerboards. The resultant linerboards were then dried and used respectively for the transportation of fresh fish. In connection with prevention of unpleasant odors of ammonia and trimethylamine typical to fresh fish, an organoleptic evaluation resulted in 5 for a blank but in 2-1 for each of the invention products.

EXAMPLE 21

In the course of a production process of toilet paper, toilet paper samples were separately impregnated at a rate of 5 g/m$^2$ with the deodorizing coating formulations of Examples 2, 6, 10 and 16. They were then dried to obtain deodorizing toilet paper samples. The toilet paper samples were used in toilets. They all gave significant effects for the elimination of unpleasant odors in both non-flush and flush toilets.

Having now fully described the invention, it will be apparent to one of ordinary skill in the art that many changes and modificaatios can be made thereto without departing from the spirit or scope of the invention as set forth herein.

We claim:

1. In a deodorizing coating formulation comprising a deodorizing ingredient, a binder resin and a liquid medium, the improvement wherein the deodorizing ingredient is a white or substantially colorless deodorizing agent composed of 10 to 90 parts by weight of a zinc compound and 90 to 10 parts by weight of an aliphatic or aromatic polycarboxylic acid or a salt thereof; wherein said zinc compound is at least one member selected from the zinc group consisting of zinc sulfate, zinc chloride, zinc phosphate, zinc nitrate, zinc carbonate, zinc acetate, zinc oxalate, zinc citrate, zinc fumarate and zinc formate, wherein said binder resin is present in said formulation in an amount of 10 to 30 wt.%.

2. In a deodorizing coating formulation comprising a deodorizing ingredient, a binder resin and a liquid medium, the improvement wherein the deodorizing ingredient is a white or substantially colorless deodorizing agent composed of 10 to 90 parts by weight of a zinc compound and 90 to 10 parts by weight of an aliphatic or aromatic polycarboxylic acid or a salt thereof; wherein said zinc compound is at least one member selected from the group consisting of zinc oxide, zinc sulfate, zinc chloride, zinc phosphate, zinc nitrate, zinc carbonate, zinc acetate, zinc oxalate, zinc citrate, zinc fumarate and zinc formate; and wherein said aliphatic or aromatic polycarboxylic acid or salt thereof is at least one member selected from the group consisting of oxalic acid, succinic acid, glutaric acid, adipic acid, pimelic acid, fumaric acid, maleic acid, methylmaleic acid, methylfumaric acid, itaconic acid, citraconic acid, mesaconic acid, acetylenic acid, methylmalic acid, isocitric acid, tartaric acid, phthalic acid, terephthalic acid, isophthalic acid, trimellitic acid, 1,2,3-benzenetricarboxylic acid, pyromellitic acid, benzenehexacarboxylic acid, naphthalenedicarboxylic acid, naphthalenetricarboxylic acid, naphthalenetetracarboxylic acid, diphenyltetracarboxylic acid, azobenzenetetracarboxylic acid and their anhydrides and salts, wherein said binder resin is present in said formulation in an amount of 10 to 30 wt.%.

3. The deodorizing coating formulation of claim 1, wherein the aliphatic polycarboxylic acid or the salt thereof is citric acid or fumaric acid, or a salt thereof.

4. The deodorizing coating formulation of claim 2, wherein the aliphatic polycarboxylic acid or the salt thereof is fumaric acid, or a salt thereof.

5. The deodorizing coating formulation of claim 1, wherein the deodorizing agent is composed of 10 to 90 parts by weight of a zinc compound and 90 to 10 parts by weight of an aromatic polycarboxylic acid or a salt thereof.

6. The deodorizing coating formulation of claim 2, wherein the deodorizing agent is composed of 10 to 90 parts by weight of a zinc compound and 90 to 10 parts by weight of an aromatic polycarboxylic acid or a salt thereof.

7. The deodorizing coating formulation of claim 5, wherein the aromatic polycarboxylic acid or the salt thereof is trimellitic acid or a salt thereof.

8. The deodorizing coating formulation of claim 6, wherein the aromatic polycarboxylic acid or the salt thereof is trimellitic acid or a salt thereof.

9. The deodorizing coating formulation of claim 1, wherein the deodorizing agent is composed of 10 to 90 parts by weight of a zinc compound and 90 to 10 parts by weight of an acidic polymer or a salt thereof.

10. The deodorizing coating formulation of claim 2, wherein the deodorizing agent is composed of 10 to 90 parts by weight of a zinc compound and 90 to 10 parts by weight of an acidic polymer or a salt thereof.

11. The deodorizing coating formulation of claim 9, wherein the acidic polymer or the salt thereof is a carboxylic acid polymer or a salt thereof.

12. The deodorizing coating formulation of claim 10, wherein the acidic polymer or the salt thereof is a carboxylic acid polymer or a salt thereof.

13. The deodorizing coating formulation of claim 1, wherein the deodorizing agent is composed of 10 to 90 parts by weight of a zinc compound and 90 to 10 parts by weight of a sulfate of aluminum.

14. The deodorizing coating formulation of claim 2, wherein the deodorizing agent is composed of 10 to 90 parts by weight of a zinc compound and 90 to 10 parts by weight of a sulfate of aluminum.

15. The deodorizing coating formulation of claim 13, wherein the sulfate of aluminum is aluminum sulfate.

16. The deodorizing coating formulation of claim 14, wherein the sulfate of aluminum is aluminum sulfate.

17. In a deodorizing coating formulation comprising a deodorizing ingredient, a binder resin and a liquid medium, the improvement wherein the deodorizing ingredient is a white or substantially colorless deodorizing agent composed of 10 to 90 parts by weight of a zinc compound and 90 to 10 parts by weight of an aliphatic or aromatic polycarboxylic acid or a salt thereof; wherein said zinc compound is at least one member selected from the zinc group consisting of zinc sulfate, zinc chloride, zinc phosphate, zinc nitrate, zinc carbonate, zinc acetate, zinc oxalate, zinc citrate, zinc fumarate and zinc formate, wherein said binder resin is present in said formulation in an amount of 10 to 30 wt.% and said binder resin is at least one member selected from the group consisting of acrylic resins, vinyl acetate base resins, and resins employed in water-base and oil-base paints and printing inks.

18. In a deodorizing coating formulation comprising a deodorizing ingredient, a binder resin and a liquid medium, the improvement wherein the deodorizing ingredient is a white or substantially colorless deodorizing agent composed of 10 to 90 parts by weight of a zinc compound and 90 to 10 parts by weight of an aliphatic or aromatic polycarboxylic acid or a salt thereof;

wherein said zinc compound is at least one member selected from the group consisting of zinc oxide, zinc sulfate, zinc chloride, zinc phosphate, zinc nitrate, zinc carbonate, zinc acetate, zinc oxalate, zinc citrate, zinc fumarate and zinc formate; and wherein said aliphatic or aromatic polycarboxylic acid or salt thereof is at least one member selected from the group consisting of oxalic acid, succinic acid, glutaric acid, adipic acid, pimelic acid, fumaric acid, maleic acid, methylmaleic acid, methylfumaric acid, itaconic acid, citraconic acid, mesaconic acid, acetylenic acid, methylmalic acid, isocitric acid, tartaric acid, phthalic acid, terephthalic acid, isophthalic acid, trimellitic acid, 1,2,3-benzenetricarboxylic acid, pyromellitic acid, benzenehexacarboxylic acid, naphthalenedicarboxylic acid, naphthalenetricarboxylic acid, naphthalenetetracarboxylic acid, diphenyltetracarboxylic acid, azobenzenetetracarboxylic acid and their anhydrides and salts, wherein said binder resin is present in said formulation in an amount of 10 to 30 wt.% and said resin is at least one member selected from the group consisting of acrylic resins, vinyl acetate base resins, and resins employed in water-base and oil-base paints and printing inks.

* * * * *